(12) United States Patent
Brodzik

(10) Patent No.: US 8,239,140 B2
(45) Date of Patent: Aug. 7, 2012

(54) SYSTEM, METHOD AND COMPUTER PROGRAM PRODUCT FOR DNA SEQUENCE ALIGNMENT USING SYMMETRIC PHASE ONLY MATCHED FILTERS

(75) Inventor: Andrzej K. Brodzik, Arlington, MA (US)

(73) Assignee: The MITRE Corporation, McLean, VA (US)

( * ) Notice: Subject to any disclaimer, the term of this patent is extended or adjusted under 35 U.S.C. 154(b) by 1070 days.

(21) Appl. No.: 11/512,163

(22) Filed: Aug. 30, 2006

(65) Prior Publication Data

US 2008/0059078 A1   Mar. 6, 2008

(51) Int. Cl.
*G06F 19/22* (2011.01)
*G06F 17/30* (2006.01)

(52) U.S. Cl. .......................................... 702/20; 707/758
(58) Field of Classification Search ........................ None
See application file for complete search history.

(56) References Cited

OTHER PUBLICATIONS

Chen, Q.-S., Defrise, M. & Deconinck, F. Symmetric phase-only matched filtering of Fourier-Mellin transforms for image registration and recognition. IEEE Transactions on Pattern Analysis and Machine Intelligence 16, 1156-1168 (1994).*
Duhamel, P. & Vetterli, M. Fast fourier transforms: A tutorial review and a state of the art. Signal Processing 19, 259-299 (1990).*
Oppenheim, A. V. & Lim, J. S. The importance of phase in signals. Proceedings of the IEEE 69, 529-541 (1981).*
Rajasekaran, S., Jin, X. & Spouge, J. L. The efficient computation of position-specific match scores with the fast fourier transform. Journal of Computational Biology 9, 23-33 (2002).*
Murphy, K. P. Biological Sequence Comparison: An Overview of Techniques. Electronic document (1994). URL http://citeseerx.ist.psu.edu/viewdoc/summary?doi=10.1.1.30.2568. 24 pages.*
Chan, F. & Rabe, E. A non-linear phase-only algorithm for active sonar signal processing. In Oceans '97. MTS/IEEE Conference Proceedings, vol. 1, 506-511 (IEEE, 1997).*
Cheever, E. A., Searls, D. B., Karunaratne, W. & Overton, G. C. Using signal processing techniques for DNA sequence comparison. In Proceedings of the 1989 Fifteenth Annual Northeast Bioengineering Conference, 173-174 (IEEE, 1989).*
Horner, J. L. & Gianino, P. D. Phase-only matched filtering. Appl. Opt. 23, 812-816 (1984).*
Rockwood, A. L., Crockett, D. K., Oliphant, J. R. & Elenitoba-Johnson, K. S. Sequence alignment by cross-correlation. Journal of Biomolecular Techniques 16, 453-458 (2005).*
A.K. Brodzik, "Phase-Only Filtering for the Masses (of DNA Data): A New Approach to DNA Sequence Alignment", IEEE Transactions on Signal Processing, Special Issue on Genomic Signal Processing, Jun. 2006.
A.K. Brodzik, "Comparative Study of Cross-Correlation Methods for Alignment of DNA Sequences Containing Repetitive Patterns", EUSIPCO Proceedings, Antalya, Turkey, Sep. 2005.

* cited by examiner

*Primary Examiner* — Marjorie Moran
*Assistant Examiner* — Soren Harward
(74) *Attorney, Agent, or Firm* — Sterne, Kessler, Goldstein & Fox PLLC

(57) ABSTRACT

Methods, systems and computer program products of DNA sequence alignment using a symmetric phase only matched filter (SPOMF) are described herein. SPOMF is useful for both global alignment and local alignment. Also described herein is a prime-length cross correlation algorithm for enhancing the robustness of the SPOMF.

12 Claims, 12 Drawing Sheets

SYSTEM, METHOD AND COMPUTER PROGRAM PRODUCT FOR DNA SEQUENCE ALIGNMENT USING SYMMETRIC PHASE ONLY MATCHED FILTERS

BACKGROUND OF THE INVENTION

1. Field of the Invention

The invention is generally related to computational genomics, and is more particularly related to DNA sequence alignment.

2. Background Art

DNA sequence alignment is one of the most important data processing tasks in computational genomics. The task appears in several applications, where efficient manipulation of large data records arranged in several different ways is required. In DNA fingerprinting, for example, an unknown collection of DNA fragments is acquired, typically few tens to few thousands of bases long. This unknown collection is then compared with one of several known collections of DNA fragments contained in a library. Either or both of these collections might be incomplete, unordered, or contain errors, including symbol insertions and symbol deletions. Finding a match between collections establishes genome identity.

A different challenge is posed by the problems of pathogen detection and gene finding. In these cases, instead of a library of known DNA fragments, a specific DNA pattern is often given. The pattern may be a part of pathogen signature or may indicate the start of a coding region. This relatively short sequence is then compared with a sequence that can be several millions of bases long. A match of the pattern with a specific region of the analyzed sequence confirms previous pathogen exposure or identifies an exon.

Related problems occur in comparative genomics and evolutionary tree reconstruction. The goal in these applications is to identify and align islands of similarity in two or more long DNA sequences. Consensus between significant parts of sequences, including coding and conserved noncoding regions, indicates functional relationship or evolutionary proximity.

Many approaches to DNA sequence alignment have been proposed over the last two decades. They include the Needleman-Wunsch (NW) algorithm, the Smith-Waterman (SW) algorithm, FASTA, BLAST, MUMmer, REPuter, and MAFFT. NW, SW, and FASTA are based on dynamic programming; BLAST utilizes a heuristic search; MUMmer and REPuter rely on suffix trees; and MAFFT performs an FFT-based cross correlation. Many other methods belong to one of these four groups. The methods vary in terms of the length of query sequence allowed, the degree of sequence similarity required, treatment of gaps, type of alignment (global or local), and speed and accuracy. Each of these methods has shortcomings, and since the amount of genomic data grows at a much faster rate than improvements in computing technology, new techniques that deliver both computational efficiency and alignment accuracy are desired.

BRIEF SUMMARY OF THE INVENTION

The present invention is directed to methods, systems and computer program products of DNA sequence alignment using a symmetric phase only matched filter (SPOMF). The SPOMF of the present invention is useful for both global alignment and local alignment. The invention also includes a prime-length cross correlation algorithm for enhancing the robustness of the SPOMF.

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 1:
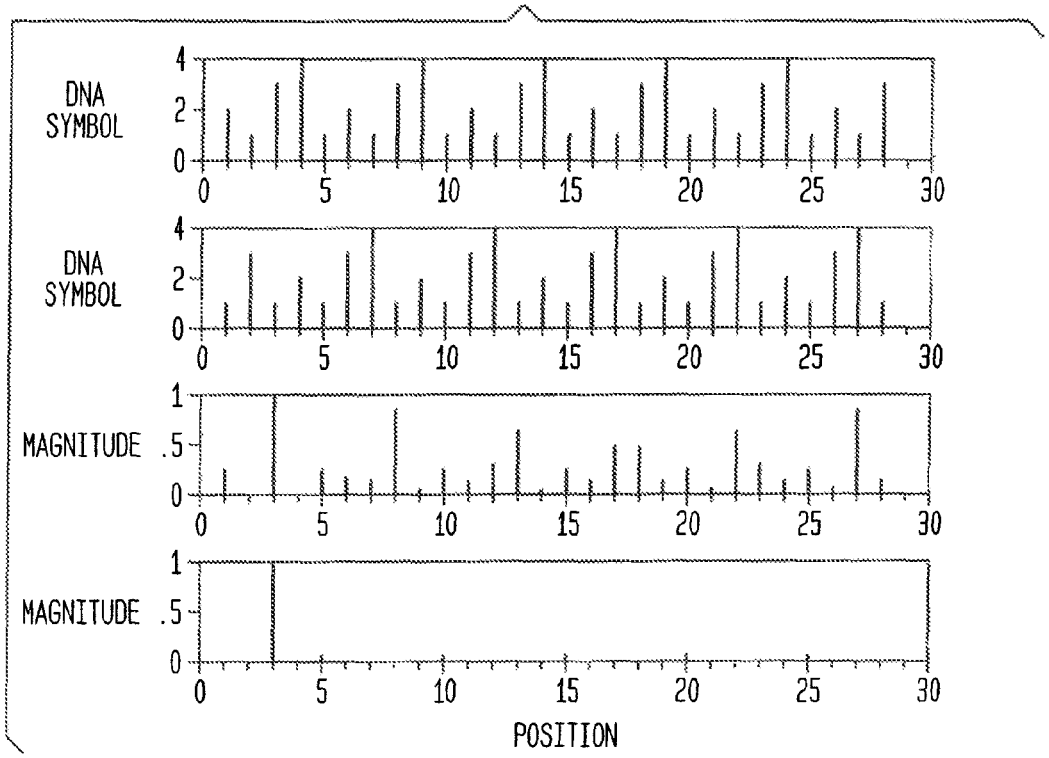
FIG. 1 compares efficacy of matched filter and symmetric phase only matched filter approaches in application to a simple four-symbol periodic sequence.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

1. Overview

Aspects of the invention are described in Andrzej K. Brodzik, "Phase-Only Filtering for the Masses (of DNA Data): A New Approach to Sequence Alignment," *IEEE Transactions on Signal Processing*, Vol. 54, No. 6, June 2006, which is herein incorporated by reference in its entirety.

Briefly stated, the invention is directed to cross correlation approaches to DNA sequence alignment. Cross correlation approaches are advantageous due to their relatively low computational complexity, which is of the order of M $\log_2$ N operations (where M and N are the lengths of library and query sequences). This is in contrast to O (MN) operations required by many sequence alignment approaches, especially the ones relying on dynamic programming and suffix trees. The conventional BLASTn and MegaBLAST algorithms (of the BLAST family) are reputed to be faster; however, complexity of these methods is difficult to evaluate since the number of computations required depends on many parameters, including the length of the seed sequence, the drop-off value for seed extension, treatment of gaps, sequence similarity, etc. Computational complexity of the cross correlation approach, on the other hand, is easily quantifiable, it does not depend on the data, and it does not have inherent limitations on the sequence size.

Conventional cross correlation approaches, such as the matched filter (MF) approach, have a number of deficiencies, including: (1) the inability to handle symbol insertions and deletions; and (2) poor performance when applied to the local alignment problem. Embodiments of the invention are directed to symmetric phase only matched filter (SPOMF) approaches, which solve these deficiencies. It is noted that SPOMF is also referred to herein as POMF (phase only matched filter).

Although, in general, the distribution of symbols in a DNA sequence might appear to be irregular, many relevant genetic phenomena can be associated with occurrence of periodically-spaced DNA symbols. Well-known examples include mutations and genetic diseases, start of a coding region, 10.5-base repeats that are due to a 3.5 amino acid repeat in alpha-helical coiled-coil regions in proteins, transposon-derived Alu repeats, and interspersed repeats occurring in multispecies conserved sequences. In fact, since DNA repeats are estimated to comprise more than one half of the human genome, most sequences of interest are likely to contain some periodic repetitions.

In the following sections, the performance gain achieved in the analysis of periodic and semiperiodic DNA data by replacing the standard cross correlation MF procedure with the phase-only cross correlation SPOMF approach of the present invention is demonstrated. First, using relatively simple models of the DNA data, we show that the MF of a periodic sequence often does not produce a unique alignment. While generally this is not an issue with SPOMF, the computation of SPOMF may be unstable in certain circumstances. Embodiments of the invention, referred to herein as prime-length cross correlation, remedy such potential instability of the SPOMF.

Subsequently, we show that MF produces large sidelobes arising from partial matches of shifts of the periodic sequence. Since magnitude of these sidelobes is proportional to the length of the sequence, the MF of a long sequence produces sidelobes that obscure the main detection peak. Conversely, the use of a SPOMF yields a greatly improved cross correlation with insubstantial sidelobes (in theory, zero sidelobes) in the case of identical sequences, and a relatively artifact-free cross correlation in case of sequences with moderate contaminations, thereby mitigating the aforementioned difficulties.

As an additional benefit of SPOMF, removal of sidelobes allows identification of detection peaks corresponding to alignments of distinct sequence segments and enables construction of a new local alignment algorithm. Accordingly, a key feature of the invention is the ability to obtain positional information about the matching segments. In other words, a key feature of SPOMF is the ability to perform local alignment. It has been often observed that the cross correlation sequence produced by the conventional MF approach does not encode positional information about misaligned segments. In the case of a single matching segment, the MF alignment peak conveys information about how much the analyzed sequence needs to be shifted to produce segment alignment, but not about the position of the segment within the sequence. In case of multiple matching segments, the difficulty is compounded, since sidelobes of the dominant segment compete with mainlobes of smaller segments. Below, we show that information about position of the segment can be easily extracted from the SPOMF sequence in a single step (i.e., without splitting the analyzed sequence into smaller sections), by identifying consecutive symbol matches in the product of the aligned sequences.

2. Matched Filter and Symmetric Phase Only Matched Filter

Define the cyclic cross correlation, or MF, of two real discrete sequences x and y by $$z(n) = x(n) * y(n) = \sum_{m=0}^{N-1} x(n+m) y(m), \quad (1)$$

$$0 \le n < N$$

where n+m is taken modulo N. Take x, y, and z to be the discrete Fourier transforms (DFTs) of x, y, and z, respectively, e.g., $$x(k) = DFT\{x(n)\} = \sum_{n=0}^{N-1} x(n) e^{2\pi i n k / N}, \quad (2)$$

$$0 \le k < N.$$

Since $$z(k) = x(k) \overline{y}(k) \quad (3)$$

(1) can be efficiently implemented by using the Fourier transformed sequences, i.e., $$z(n) = DFT^{-1}\{x(k) \overline{y}(k)\}, \quad (4)$$

where computation of each DFT requires N $\log_2$ N operations.

The SPOMF of two discrete sequences x and y is given by the formula $$w(n) = DFT^{-1}\left\{\frac{x(k) \overline{y}(k)}{|x(k) \overline{y}(k)|}\right\}, \quad (5)$$

$$x(k) \text{ and } \overline{y}(k) \ne 0.$$

3. Regular Periodic DNA Sequences

DNA sequence is a symbolic string of characters 'a', 'c', 'g', and 't' denoting the four nucleotides that make up the genetic code: adenine, cytosine, guanine, and thymine. Various methods of mapping a symbolic DNA sequence to a numeric sequence have been proposed, including the use of complex and hypercomplex number systems. For convenience, in the next two sections we will consider only single-symbol DNA sequences represented by binary numbers, although the invention is not limited to this example illustration. Furthermore, we will only consider periodic sequences (in the sense specified below) although again the invention is not limited to this example illustration. In Section 5 we apply the developed formalism to the four-symbol DNA data and discuss processing of semiperiodic and nonperiodic DNA sequences.

Definition 1: Take $N, P, S \in Z^+$, such that $P$ is a divisor of $N$, and $0 \leq S < N$. A regular $P$-periodic comb shifted by $S$ is an $N$-point sequence $$x_{N,P,S}(n) = \begin{cases} 1, & (n-S) \equiv 0 \pmod{P} \\ 0, & \text{otherwise} \end{cases} \quad (6)$$

We have $x_{N,P,S} = x_{N,P,S} \mod P$. The first result shows that if $x(n)$ is a comb, then its DFT, $x(k)$ is also a comb.

Theorem 1: Take $N, P, S \in Z^+$ such that $\bar{P} = N/P \in Z$, $0 \leq S < P$. The Fourier transform of an $S$-shift of a $P$-periodic comb $x_{N,P,S}$ is a scaled and modulated $\bar{P}$-periodic comb $\bar{P}e^{2\pi i k S/N}x_{N,\bar{P}}$.

Proof:

$$x_{N,P,S}(k) = \sum_{n=0}^{N-1} x_{N,P,S}(n) e^{2\pi i n k/N}$$

$$= e^{2\pi i k S/N} \sum_{s=0}^{P-1} e^{2\pi i s k/P},$$

$$= \begin{cases} \bar{P}e^{2\pi i k S/N}, & k \equiv 0 \pmod{\bar{P}} \\ 0, & \text{otherwise.} \end{cases}$$

We are now ready to compute the MF and SPOMF of regular combs.

Theorem 2: The MF of a regular $P$-periodic comb $x_{N,P,S}$ is a $P$-periodic comb $$z(n) = \begin{cases} \bar{P}, & (S-n) \equiv 0 \pmod{\bar{P}} \\ 0, & \text{otherwise} \end{cases} \quad (7)$$

Proof: Using Theorem 1 and (4), we have $$z(n) = \frac{1}{N} \sum_{k=0}^{N-1} e^{-2\pi i n k/N} x(k) \bar{y}(k) = \frac{\bar{P}^2}{N} \sum_{l=0}^{P-1} e^{2\pi i l(S-n)/P}$$

which leads to (7).

Theorem 2 shows that the MF of a regular comb provides a measure of DNA sequence misalignment, provided $S<P$, which is of limited use. Due to Theorem 1, the SPOMF of a regular comb is not defined, since insertion of $x_{N,P}$ into (5) results in division by zero. According to an embodiment of the invention, this issue is resolved by assigning to the "divide by zero" points some small fixed value. Like the MF, however, SPOMF may provide a measure of DNA sequence misalignment only when $S<P$. Moreover, there is a performance penalty associated with zeroes of the DFT of a comb, manifesting itself in sidelobes of the cross correlation sequence. As will be shown in the next section, embodiments of the invention address these obstructions by restricting the length of the comb to a prime number (such resulting algorithms are referred to herein as prime-length cross correlation algorithm).

4. Irregular Periodic DNA Sequences

Definition 2: Take $N, P, S \in Z^+$, $N$ an odd prime. An irregular $P$-periodic comb shifted by $S$ is an $N$-point sequence $$x'_{N,P,S}(n) = \begin{cases} 1, & (n-S) \equiv 0 \pmod{\bar{P}} \\ 0, & \text{otherwise} \end{cases} \quad (8)$$

The restriction of $N$ to primes is not very severe. For example, there are 25 primes between 1 and 100, 21 primes between 101 and 200, and 18 primes between 201 and 300, all of them fairly uniformly distributed. Moreover, as with the power-of-two length DFT, there are fast algorithms for computing a prime length DFT. We will consider the DFT of an irregular comb next.

Theorem 3: Take $N, P, S \in Z^+$, $N$, an odd prime. The Fourier transform of an irregular $P$-periodic comb $x_{N,P,S}$ is $$x'_{N,P,S}(k) = \begin{cases} \lfloor \frac{N}{P} \rfloor + 1, & k = 0 \\ \frac{1 - \exp(2\pi i k P(\lfloor N/P \rfloor + 1)/N)}{1 - \exp(2\pi i k P/N)} e^{2\pi i k S/N}, & \text{otherwise} \end{cases} \quad (9)$$

where $\lfloor N/P \rfloor$ is the largest integer not greater than $N/P$.

Proof: We have $$x'_{N,P,S}(k) = \sum_{n=0}^{N-1} x'_{N,P,S}(n) e^{2\pi i n k/N}$$

$$= e^{2\pi i k S/N} \sum_{s=0}^{\lfloor \frac{N}{P} \rfloor} e^{2\pi i s k P/N}$$

which leads to (9).

Corollary 1: $x'_{N,P,S}(k) \neq 0 \forall k$

Proof: Follows directly from Theorem 3.

In effect, by selecting a prime $N$, the zero obstruction is removed. The next result characterizes performance of the MF of an irregular comb.

Theorem 4: Set $\delta = \lfloor N/P+1 \rfloor$. The MF $z'$ of an irregular $P$-periodic comb $x_{N,P,S}$ is given by $$z'(n) = \frac{\delta^2}{N} + \frac{1}{N} \sum_{k=1}^{N-1} e^{2\pi i k(S-n)/N} \frac{1 - \cos(2\pi k P \delta/N)}{1 - \cos(2\pi k P/N)}. \quad (10)$$

The mainlobe of $z'$ is given by $$M = z'(n=S) = \delta \quad (11)$$

and the largest sidelobe of z' is given by $$S=z'(n=S+P)=\delta-1 \quad (12)$$

Proof: Equation (10) follows directly from inserting $x'_{N,P,S}$ and the conjugate of $x'_{N,P}$ (Theorem 3) into (4). Equation (11) follows from (1) and (8). To obtain (12), take $$M - S = \frac{1}{N}\sum_{k=1}^{N-1}(1-e^{-2\pi ikP/N})\frac{1-\cos(2\pi k\delta P/N)}{1-\cos(2\pi kP/N)}$$

$$= \frac{1}{N}\sum_{k=1}^{N-1}[R(k)+iI(k)]$$

where $$R(k) = 1 - \cos(2\pi k\delta P/N)$$

and $$I(k) = -\sin\{2\pi kP/N\}\frac{1-\cos(2\pi k\delta P/N)}{1-\cos(2\pi kP/N)}.$$

Since $I(k) = -I(N-k)$ for $1 \leq k \leq (N-1)/2$, then $\sum_{k=1}^{N-1} I(k) = 0$.

Moreover, we have $\sum_{k=1}^{N-1} R(k) = \sum_{k=1}^{N-1}[1-\cos(2\pi k\delta P/N)] = N$.

In effect $S=M-(M-S)=\delta-1$.

The performance of the MF of an irregular comb is summarized by the following corollary.

Corollary 2: The ratio of the mainlobe to the largest sidelobe of the MF of an irregular P-periodic comb is given by $$\frac{z'(S)}{z'(S+P)} = \frac{\delta}{\delta-1}. \quad (13)$$

The next result characterizes the performance of SPOMF of an arbitrary nontrivial prime length binary sequence, which includes the case of an irregular P-periodic comb.

Theorem 5: Take N to be an odd prime number and S to be an integer $0 \leq S<N$. The SPOMF of an N-point binary sequence, shifted by S, that is not all-zero or all-one, is given by $$w'(n) = \begin{cases} 1, & n = S \\ 0, & \text{otherwise} \end{cases} \quad (14)$$

Proof: The conditions x(n) is not all-zero or all-one and N is an odd prime guarantee that $x(k)\neq 0\forall_k$. Then, it follows from (5) and from the shift property of the Fourier transform that $$w'(n) = \frac{1}{N}\sum_{k=0}^{N-1} e^{-2\pi ikn/N}\frac{x(k)\overline{y(k)}}{|x(k)\overline{y(k)}|}$$

$$= \frac{1}{N}\sum_{k=0}^{N-1} e^{2\pi ik(S-n)/N}$$

$$= \begin{cases} 1, & n = S \\ 0, & \text{otherwise} \end{cases}.$$

As can be seen from Theorems 4 and 5, when the DNA sequence is an irregular P-periodic comb, then the SPOMF significantly outperforms the MF. While the SPOMF yields a greatly improved cross correlation sequence, the MF gives rise to sidelobes, the largest of which approaches the magnitude of cross correlation mainlobe as N increases and P remains constant. Conversely, decreasing the length of the P-periodic comb and maintaining a constant period reduces the sidelobes of the MF cross correlation sequence. Since a real DNA sequence is never purely periodic, and many sequences contain a limited number of symbol repeats (although some repeats are always present in a sufficiently long sequence due to the roughly equal distribution of symbols a, c, g, and t, and the three-base encoding of amino acids in exons), a question arises as to how the performance of a MF algorithm scales with the decreasing content of periodic symbols. This question is not easy to answer, in part because of the difficulty of defining the opposite of a periodic sequence. Although many authors contrast occurrence of patterns with random symbol distribution, this is not a true dichotomy; moreover, it is questionable whether the distribution of symbols in a DNA sequence can ever be random. A more suitable definition of a nonperiodic binary sequence might include a rule requiring the difference between positions of any two symbols to be unique. An additional constraint could be added that this set of differences be exhaustive. We can state this more formally as follows.

Definition 3: An N-point binary sequence $x_0, \ldots, x_i, \ldots, x_j, \ldots, x_{N-1}$ having 2 $2 \leq L<N$ nonzero elements is nonperiodic, iff for all distinct pairs of nonzero elements and $x_i$ and $x_j$, $i\neq j$, the set of values $(i-j)(\text{mod } N)$ is identical with the set of integers $1 \leq k \leq N$.

Definition 3 is in fact used in the construction of special sequences having an ideal two-valued autocorrelation $$z'(n) = \begin{cases} L, & n = 0 \\ 1, & \text{otherwise} \end{cases} \quad (15)$$

These special sequences are known as modular Golomb rulers in communications, and as cyclic difference sets (CDS) in combinatorics. Simple examples of CDS include the sequences '0110100' and '1 101 000 001 000'. In general, CDS are not easy to obtain, and for many sequence sizes, CDS do not exist. For example, the CDS given above are the only ones for a seven- and a 13-base sequence. The scarcity of CDS implies that perfectly irregular DNA sequences are relatively rare, and therefore most DNA sequences can be considered semiperiodic.

Equipped with the concept of CDS as a model for a nonperiodic sequence, the two cross correlation approaches can be more easily compared. From Theorem 5, the SPOMF of any binary sequence (including periodic and nonperiodic sequences), for which it can be defined, yields a greatly improved (perfect or near perfect at times) cross correlation. Assuming a fixed frequency of DNA symbols, the MF of a periodic sequence yields a cross correlation with the ratio M/S tending to infinity as N increases. In contrast, the MF of a nonperiodic sequence yields a two-valued cross correlation, with the ration M/S tending to infinity as N increases. When a sequence is neither periodic nor nonperiodic, it is called semiperiodic. In general, a semiperiodic sequence might contain multiple segments, some periodic and some irregular. In a simplified model, a semiperiodic sequence will contain only two segments: a truncation of a periodic sequence and a cyclic difference set (when it exists). Since performance of the MF of a nonperiodic sequence is optimal, cross correlation of a semiperiodic sequence can be expected to depend mainly on the length of its periodic component. This prediction has been confirmed by experiments; the results indicate that sidelobes of the MF decrease when sequences become more irregular, and that performance of the two methods becomes comparable when sequences have no obvious periodic component.

5. Comparison of SPOMF and MF

In this section, we give examples of SPOMF and MF of several synthesized and real DNA sequences of increasing complexity. To illustrate the theoretical results of the previous section, we begin with cyclically shifted, purely periodic sequences. Later, we investigate cross correlations of linearly shifted semiperiodic sequences and test robustness of the SPOMF approach to single and multiple symbol insertions and deletions, and symbol mismatches.

Since the intention here is to provide a proof of concept for the SPOMF approach and to illustrate the key aspects of the alignment problem in a manner that facilitates visual inspection, most examples are limited to relatively short sequences, although the invention is not limited to these examples. The small size of the sequences does not limit the generality of the examples, since in practice DNA data is often processed in segments of a few hundred to a few thousand bases at a time. The examples include moderately homologous sequences (50%-100% homology), which are typical in many applications, including cross-species sequence comparisons. In the later part of Section 5-B and in Section 5-C, where the construction of a more local alignment algorithm is discussed, two examples of more complex DNA sequences are given, the second one having no significant periodic component.

The implicit focus to this point has been on global sequence alignment. This section will begin with examples of a global alignment, and then it will gradually progress toward the more general case (in the sense explained below) of a local alignment.

The goal of the global alignment is to maximize the total number of symbol matches in the two sequences, regardless of the relative position of symbols within the sequence. For example, when sequences are long and not closely related, then the matching symbols are likely to be distributed throughout the sequence. In contrast, the goal of the local alignment is to identify a smaller section of the sequence that contains a large number of matching symbols, even if the number of matching symbols in that section is less than the number of matching symbols in the entire sequence (in the global alignment). In general, there might be more than one region of this type, and the distance between these regions in two sequences might be not preserved. In such a case multiple local alignments need to be performed. Moreover, in both local and global alignments, symbol insertions or deletions (the so-called indels) in the sequences might be allowed, thereby blurring the distinction between the two alignments.

Herein, we will adopt a narrow definition of the local alignment. We will assume that indels can occur between matching regions, but not within a region, and that matching symbols within a region are consecutive. This assumption will significantly simplify analysis of the results. However, the invention is not limited to this condition.

A. Synthesized Data

Example 1

In the first experiment, the two approaches were applied to a composite, four-symbol periodic sequence, consisting of five individual combs, $x_{29,5}$. The constituent a, c, g, and t sequences were chosen to create a repetitive pattern "acagt" (plot 102 in FIG. 1). The query sequence was identical to the cyclicly shifted by three symbols library sequence $y_{29,5} = x_{29,5,3}$ (plot 104 in FIG. 1; the indexes of x are as in definition 1). The symbols "a", "c", "g", and "t" were marked in the plots with stems equal to 1, 2, 3, and 4, respectively. The cross correlations shown (plots 106 and 108 in FIG. 1) are the sums of cross correlations performed on individual symbol sequences.

The use of SPOMF produced a perfect cross correlation sequence with no sidelobes. The use of MF produced a cross correlation sequence with a peak at n=S=3, equal to $\delta = \lfloor 29/5 \rfloor + 1 = 6$, and multiple sidelobes. The largest sidelobe was equal to $\delta - 1 = 5$ and occurred at n=S+P=8, as predicted by Theorem 4. The magnitudes of MF and SPOMF sequences shown in FIG. 1 (and subsequently) were normalized to facilitate visual comparison of results.

Example 2

Figure 2:
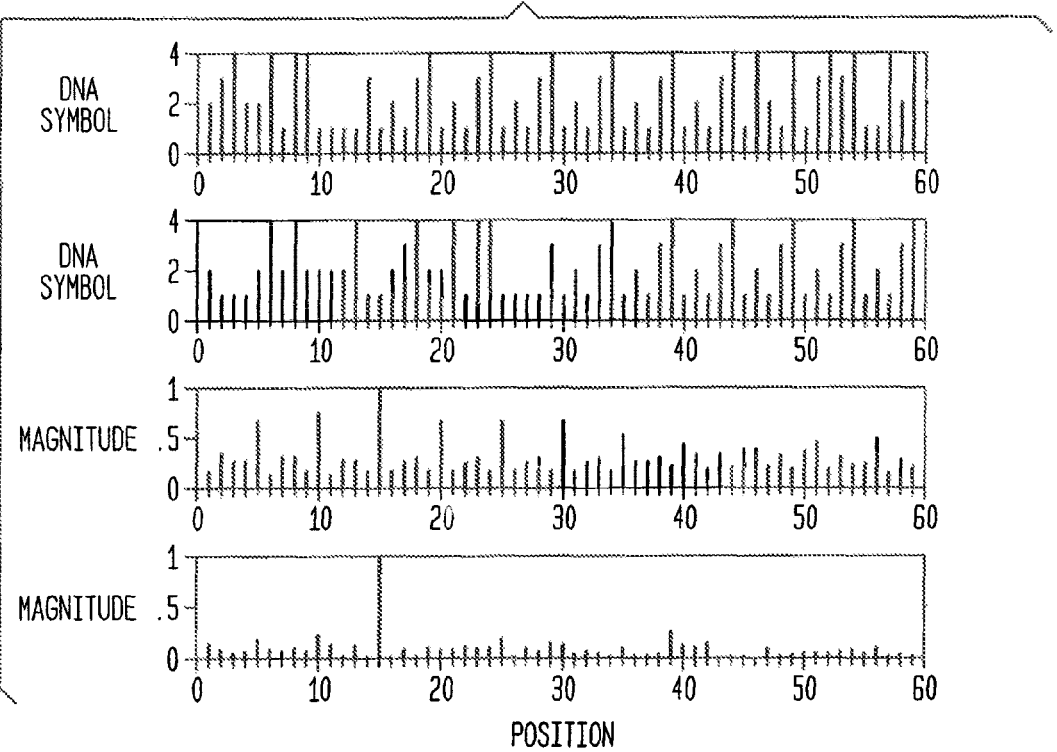
FIG. 2 illustrates alignment of semiperiodic DNA sequences containing a repetitive pattern, random symbols, and a mismatching segment.

The first experiment has shown an example of sequence alignment performed on purely periodic, perfectly matched data. In practice, in addition to periodic motifs, DNA sequences often contain segments of irregularly distributed symbols and segments that do not match. FIG. 2 shows an example of such a case. The two misaligned sequences $x_{61}$ and $y_{61}$ share a 46-base segment, the first 16 bases of which are random, while the remaining 30 bases contain a repetitive pattern "acagt". The library sequence $x_{61}$ is appended by a random 15-base segment, and the query sequence $y_{61}$ is concatenated to a different random 15-base segment. In effect, $x_{61}$ and $y_{61}$ are misaligned by 15 bases, and mismatched (when aligned) at 15 bases. The cross correlation peak in both MF and SPOMF occurs at n=S=15. While due to the 15-base segment mismatch the SPOMF sequence does not produce an ideal cross correlation sequence in this case, its sidelobes are significantly smaller than the sidelobes of the MF (the largest sidelobe of SPOMF equal to 0.238 occurs at n=39, and the largest sidelobe of MF equal to 0.736 occurs at n=10).

B. Real Data

In the second part of this section, we describe experiments performed on two real DNA sequences selected from GenBank: *Mus musculus* BAC clone RP23-1116, locus AC098708, bp 46 101:46 502 (x401 and y401), and *Mus musculus*, chromosome 9, locus AC103610, bp 143 101:144 114 (x523 and y523). Both DNA sequences contained about 200-base-long segments of three-to-six-bases-long repetitive patterns of two (a and g) or three (a, c and g) symbols. Insertions and deletions were not part of the original data but were induced artificially. MF and SPOMF computations in all experiments were performed using a linear cross correlation of length that was twice the length of the analyzed sequence; however, to facilitate visual comparisons, only the relevant half of the cross correlation sequence samples is shown in the plots.

Example 3

Figure 3:
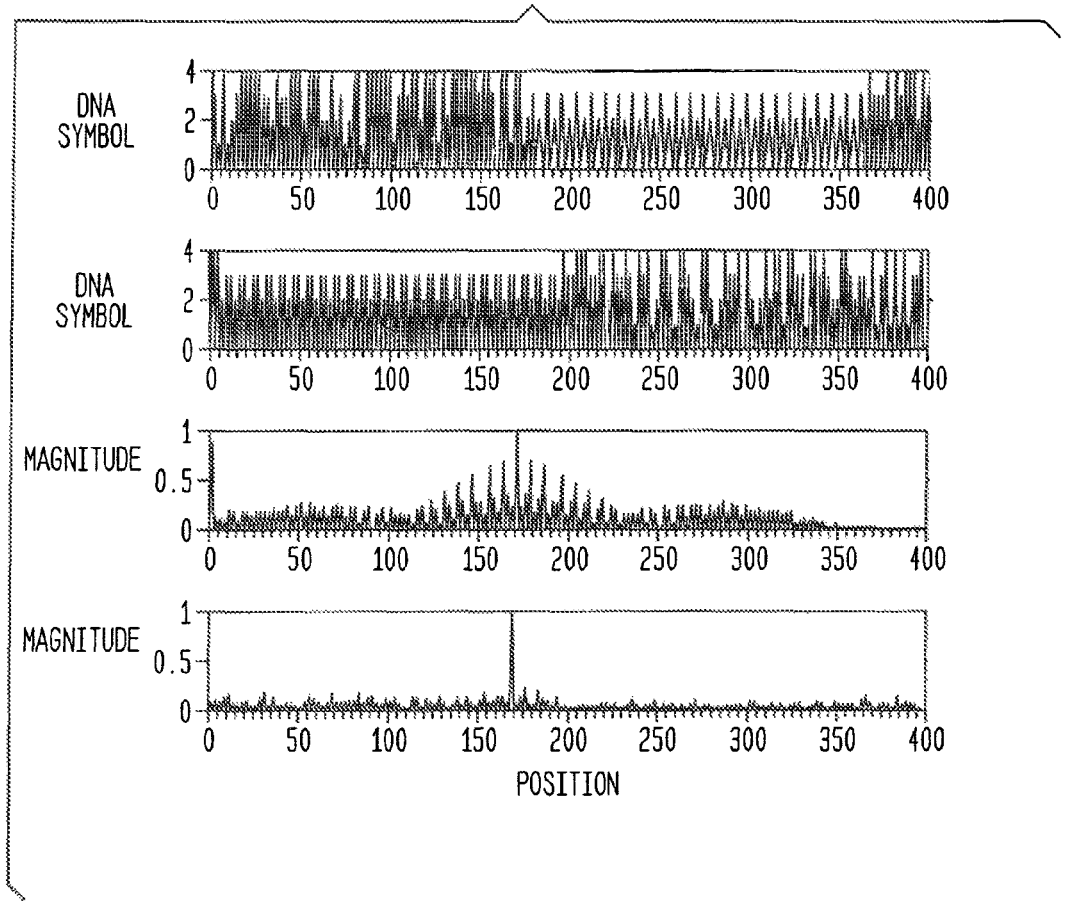
FIG. 3 illustrates alignment of semiperiodic contiguous DNA sequences containing a 190-base repetitive segment, GenBank AC098 708.

In the first experiment of this subsection, we have analyzed two linearly shifted sequences x401 and $y401 = x_{401\ 170}$, derived from the GenBank sequence AC098 708. The sequences contained 231 contiguous matching symbols, including a 190-base repetitive pattern "accagg", and 170 mismatching symbols. No deletions or insertions were applied to the sequences. The MF approach produced a cross correlation sequence having the ratio of magnitudes of the largest sidelobe (occurring due to a partial match of the shifted pattern) and the mainlobe equal to 0.69. The SPOMF approach produced a cross correlation sequence having the ratio of magnitudes of the largest sidelobe (occurring due to a 170-base segment mismatch) and the mainlobe equal to 0.19 (FIG. 3).

Example 4

In the previous experiment, the matching symbols in the two sequences were contiguous. In many practical applications, the matching segments may contain contaminations, including symbol insertions, deletions and substitutions. This situation is addressed in this experiment.

Figure 4:
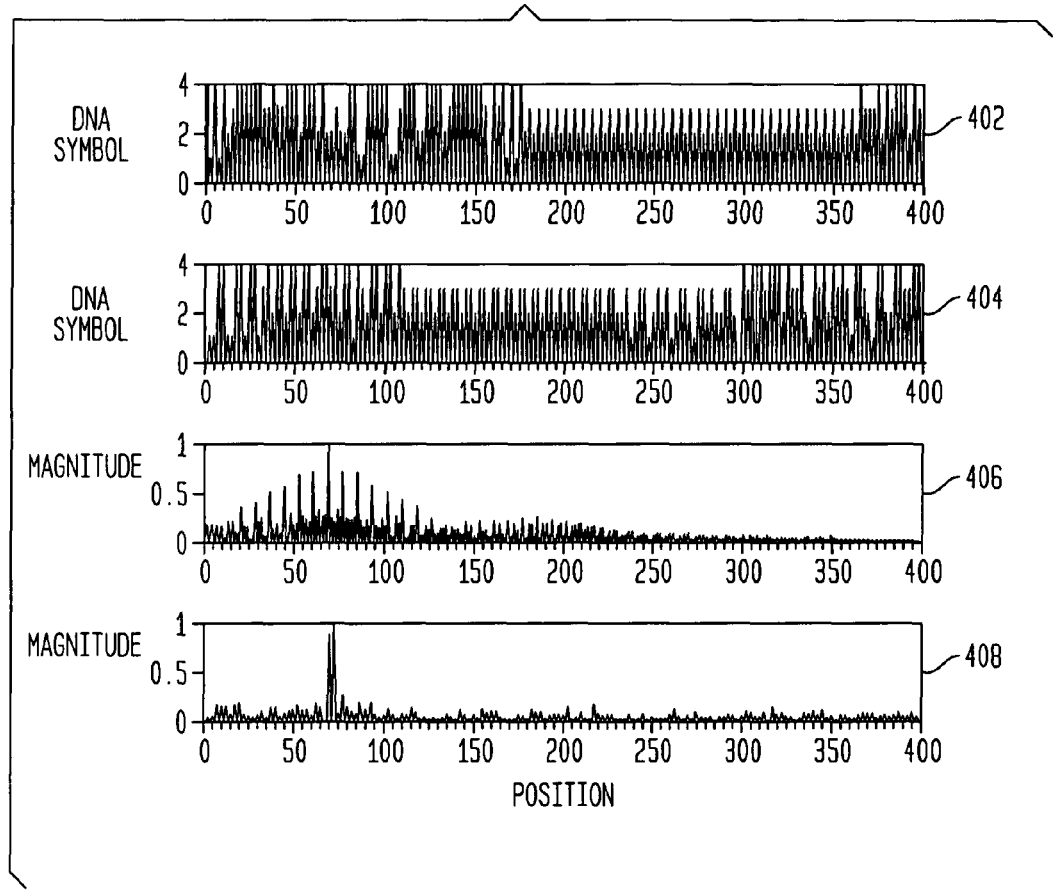
FIG. 4 illustrates alignment of semiperiodic DNA sequences containing a 190-base repetitive segment preceded by a symbol deletion, GenBank AC098 708.

The sequences $x_{401}$ and $y_{401}$ (plots 402 and 404 in FIG. 4) are similar to the ones used in the previous experiment, except for two modifications. First, the second sequence was shifted by 70 symbols rather than by 170 symbols with respect to the first sequence ($y_{401}=x_{401,70}$). This produced a matching segment containing a significant number of both repetitions and irregular symbols. Second, the sequence $x_{401}$ was modified by a deletion of three symbols at bp 177:179 (the number of consecutive deletions is irrelevant here, except for providing a more convenient display of alignment results). The deletion effectively split the library sequence $x_{401}$ into two segments. The shorter one (105 bases) was comprised of a largely random DNA symbol assembly. The longer one (220 bases) was comprised mostly of a complex repetitive motif with a predominance of symbols "c" and "g".

In effect, a perfect (global) alignment of the entire 331-base segment was impossible, i.e., either only the sequence segment prior to the deletion could be matched (in one local alignment), or only the sequence segment following the deletion could be matched (in another local alignment). To identify both segments, the cross correlation sequence needs to produce two distinct peaks. Both approaches do produce two such peaks: one at n=70 and one at n=73. However, while the two peaks can be clearly identified in the SPOMF plot (magnitudes 0.9 and 1.0, plot 408 in FIG. 4), in the MF plot, the peak corresponding to the second alignment is much smaller (magnitude 0.19, plot 406 in FIG. 4) and is obscured by multiple large sidelobes.

Example 5

In the third experiment, a more elaborate case of noncontiguous matching segments was considered. Two linearly shifted sequences $x_{523}$ and $y_{523}=x_{523,60}$, derived from the GenBank sequence AC103610, were used. The matching 463 bases included both repetitive and irregular symbols. While in Example 4, only one of the sequences had an insertion, here each sequence contained a unique insertion: $x_{523}$ had a five-symbol insertion at n=21, and $y_{523}$ had a five-symbol insertion at n=401. As in experiment 4, the insertions had an effect of splitting the sequences into two matching segments. Unlike in experiment 4, however, one of the segments contained a gap. The case can be best explained symbolically. Take as the first sequence the string "$a_1 xbbba_2 a_2$" and as the second sequence the string "$a_1 bbbxa_2 a_2$", where x denotes deletion, and $a_1$, $a_2$, and b are arbitrary symbols. Both sequences contain two identical segments, i.e., "bbb" and "$a_1 \ldots a_2 a_2$". However, the second segment is not contiguous. This is illustrated in more detail in FIG. 6. The first segment (in the middle of the sequence, marked with a bar in the second plot) is comprised mostly of periodic repetitions of symbols "a" and "g". The second composite segment (having one component at the beginning of the sequence, and another component in the later part of the sequence, marked with bars in the third plot) is comprised of an assembly of mostly irregular DNA symbols.

Figure 5:
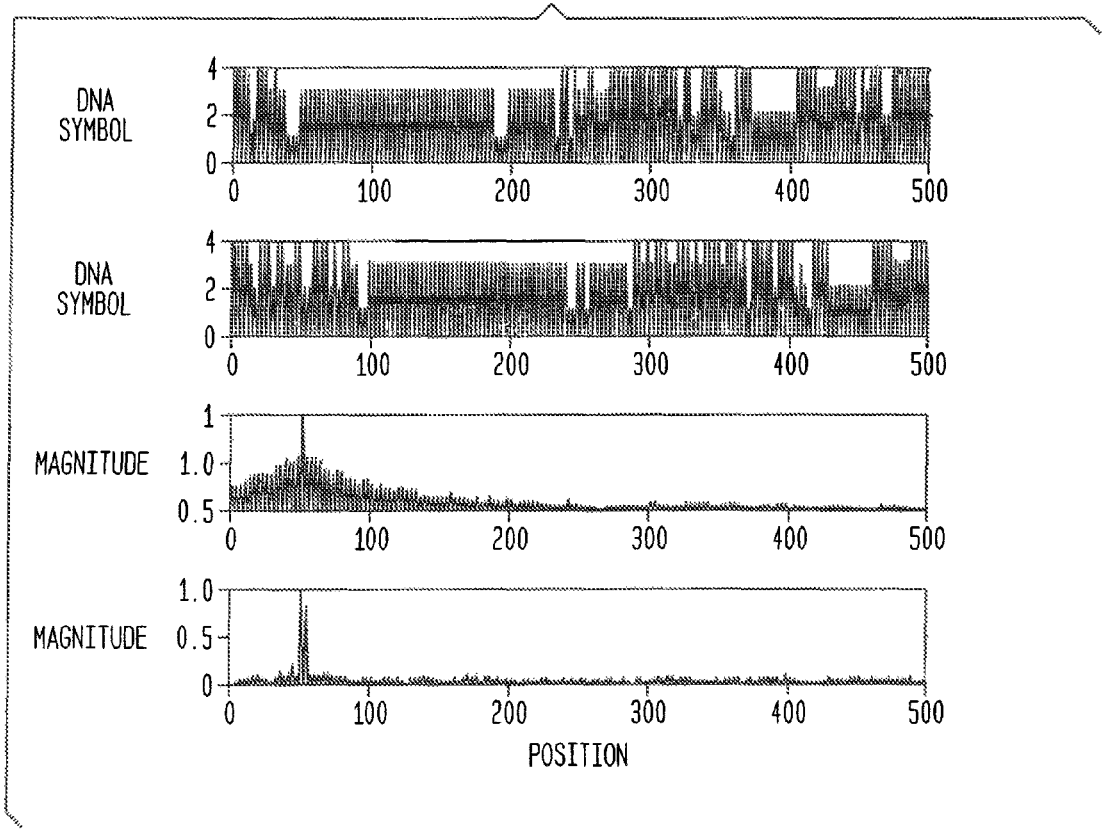
FIG. 5 illustrates alignment of semiperiodic DNA sequences with symbol insertions, GenBank AC103 610.

Alignments of both segments can be easily discerned in the SPOMF sequence (detection peaks at n=55 and at n=60 of magnitude 1.0 and 0.843, respectively, in plot 508 of FIG. 5). Note, that SPOMF detects both segments, even though the second segment is noncontiguous and nonperiodic. In contrast, only one of the alignments can be identified in the MF sequence (a detection peak at n=55 in plot 506 of FIG. 5). The second alignment in the MF sequence (at n=60, equal to 0.531) is obscured by sidelobes. Moreover, the MF produces an anomalous correlation peak (the second largest in the correlation sequence, at n=43) that corresponds to a shift of the first segment (plot 608 of FIG. 6).

C. Local Alignment

The results of the experiments warrant several observations. The robustness of the SPOMF method to partial matches of shifts of periodic DNA segments results in the removal of sidelobes and an improved readability of the SPOMF cross correlation plot. Removal of sidelobes is particularly important in the analyses of multicomponent sequences. Multicomponents occur, for example, when a contiguous matching segment becomes contaminated by a symbol deletion or insertion. The segment may then be partitioned into several components, each requiring a separate local alignment. Since the SPOMF sequence does not produce anomalous partial match sidelobes, peaks of the SPOMF cross correlation sequence can be associated with these local alignments.

Figure 6:
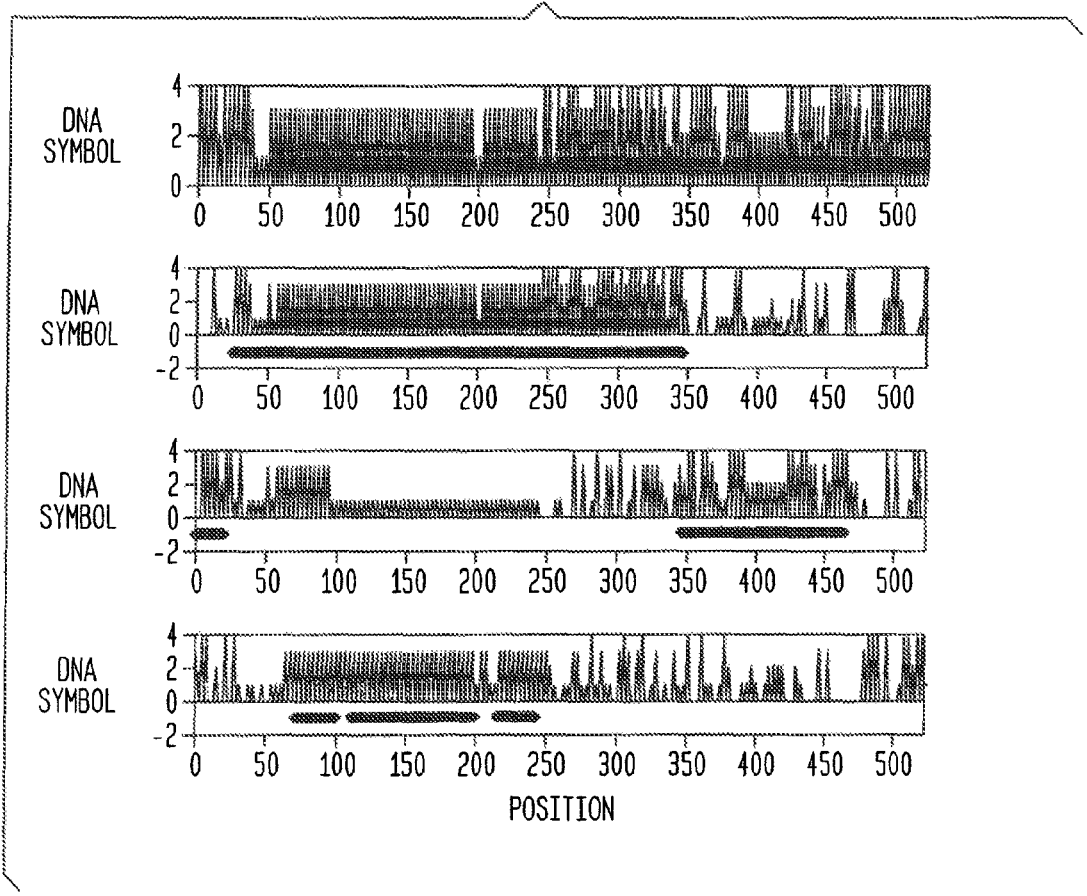
FIG. 6 illustrates alignment of semiperiodic DNA sequences with symbol insertions, GenBank AC103 610.
Figure 13:
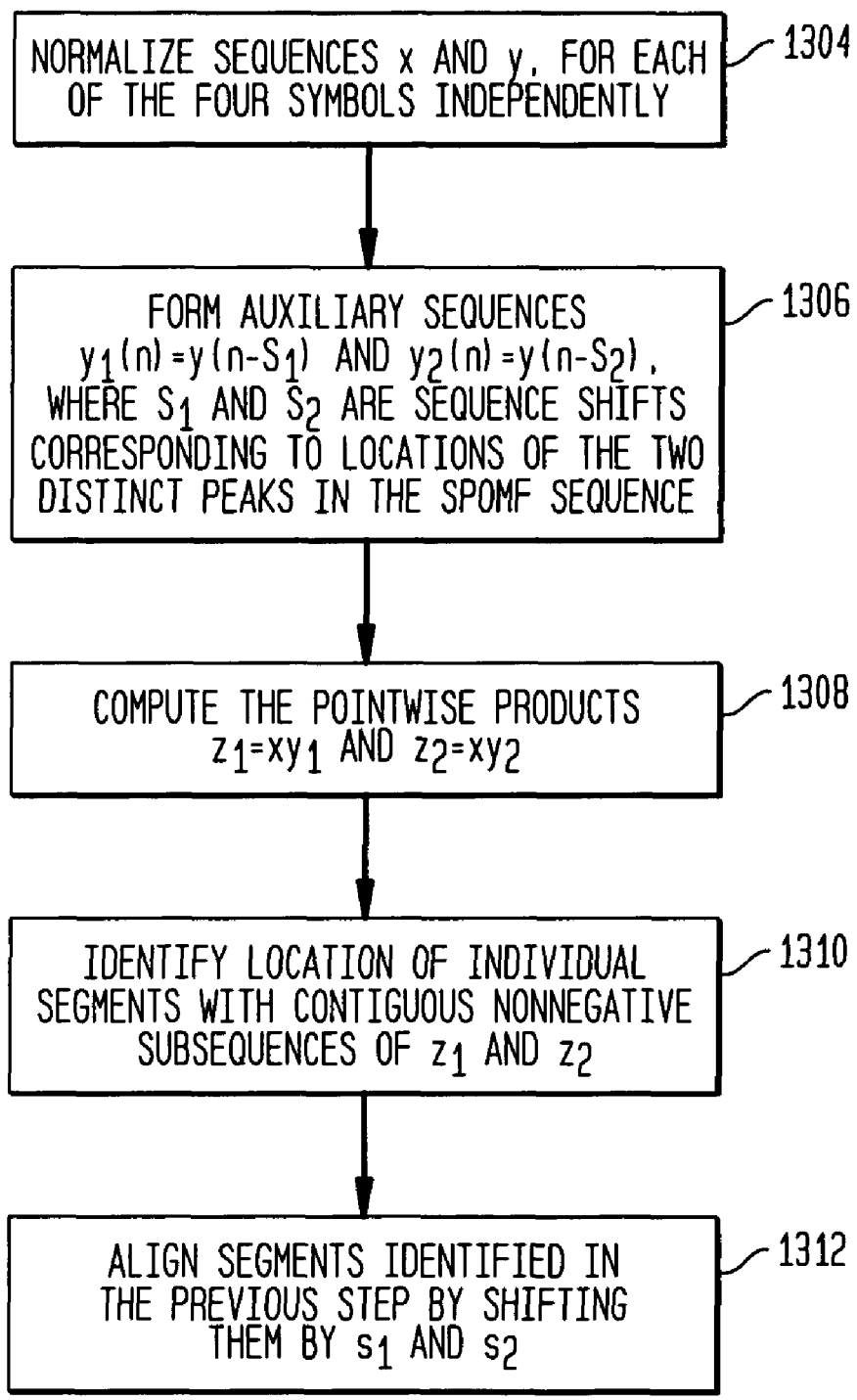
FIG. 13 illustrates a local alignment process using a symmetric phase only matched filter, according to an embodiment of the invention.

The decomposition of $y_{523}$ in the last experiment into two almost orthogonal subsequences (FIG. 6, plots 604 and 606) corresponding to the two distinct peaks of the SPOMF sequence (FIG. 5, plot 508) suggests that not only can local alignment of the individual segments be performed using SPOMF, but positional information about the individual segments within a sequence can be extracted as well. FIG. 13 illustrates a local alignment process according to an embodiment of the invention. The steps of FIG. 13 are performed after SPOMF has been performed on sequences x and y (in other words, the steps of FIG. 13 are performed after Eq. (5) has been performed on sequences x and y).

In step 1304, sequences x and y are normalized, for each of the four symbols independently.

In step 1306, auxiliary sequences $y_1(n)=y(n-S_1)$ and $y_2(n)=y(n-S_2)$ are formed, where $S_1$ and $S_2$ are sequence shifts corresponding to locations of the two distinct peaks in the SPOMF sequence.

In step 1308, the pointwise products $z_1=xy_1$ and $z_2=xy_2$ are computed.

In step 1310, the location of individual segments with contiguous nonnegative subsequences of $z_1$ and $z_2$ is identified.

In step 1312, segments identified in the previous step are aligned by shifting them by $S_1$ and $S_2$.

Normalization replaces the assignment of binary values, marking symbol occurrence at a given position in a sequence, with an assignment of some positive/negative values (that depend on the total count of symbols in the sequence). If symbols match, then all four sequences, $z_a$, $z_c$, $z_g$, $z_t$, are positively valued. Conversely, if symbols mismatch, then two of the four sequences are negatively valued. In effect, detection of a symbol mismatch is equivalent to the identification of a negatively valued sequence. Note, that the normalization step is included here to facilitate visual evaluation of the alignment, but is not essential in the algorithm.

Figure 7:
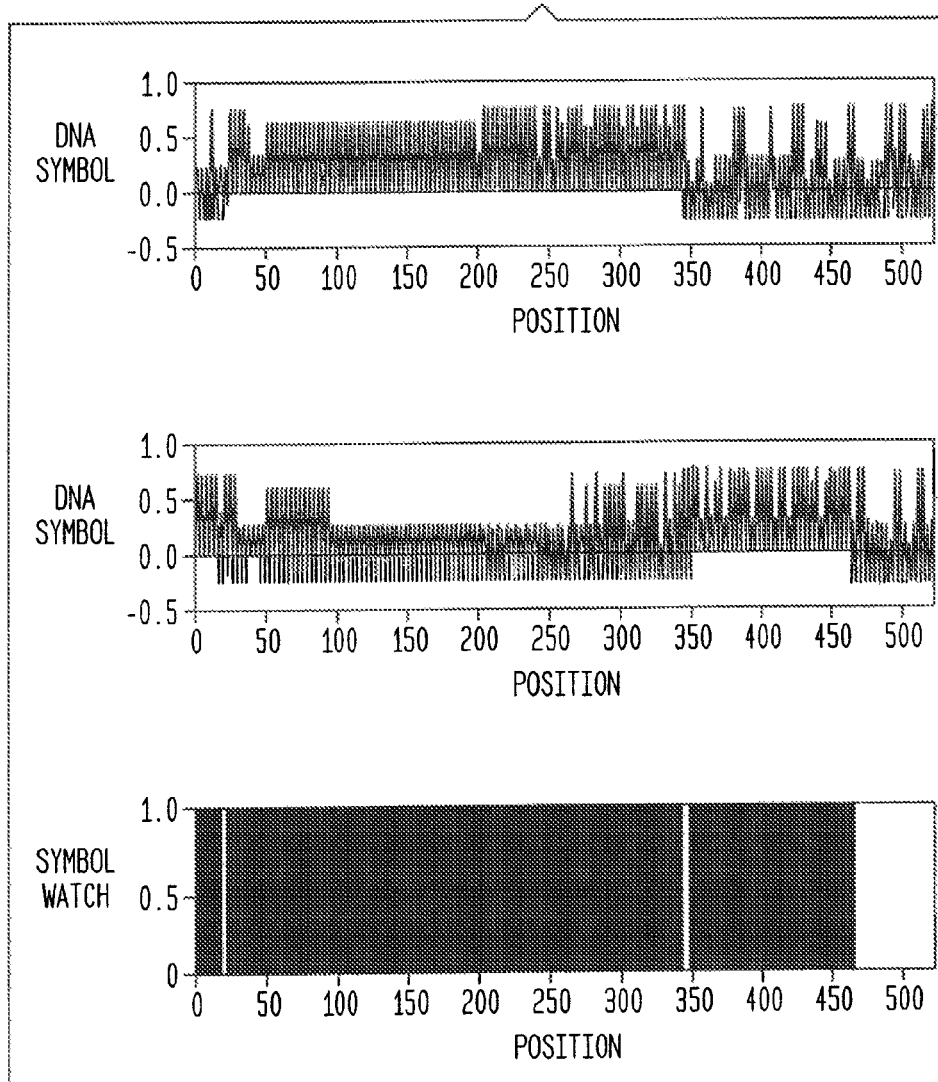
FIG. 7 illustrates plots relating to local alignment.

Results of the processing are illustrated in FIG. 7. An important advantage of this procedure is that it does not rely on windowing, and therefore resolution of the positional information is not limited by the window width. Further details of the implementation of the algorithm are given elsewhere herein.

Example 6

Figure 8:
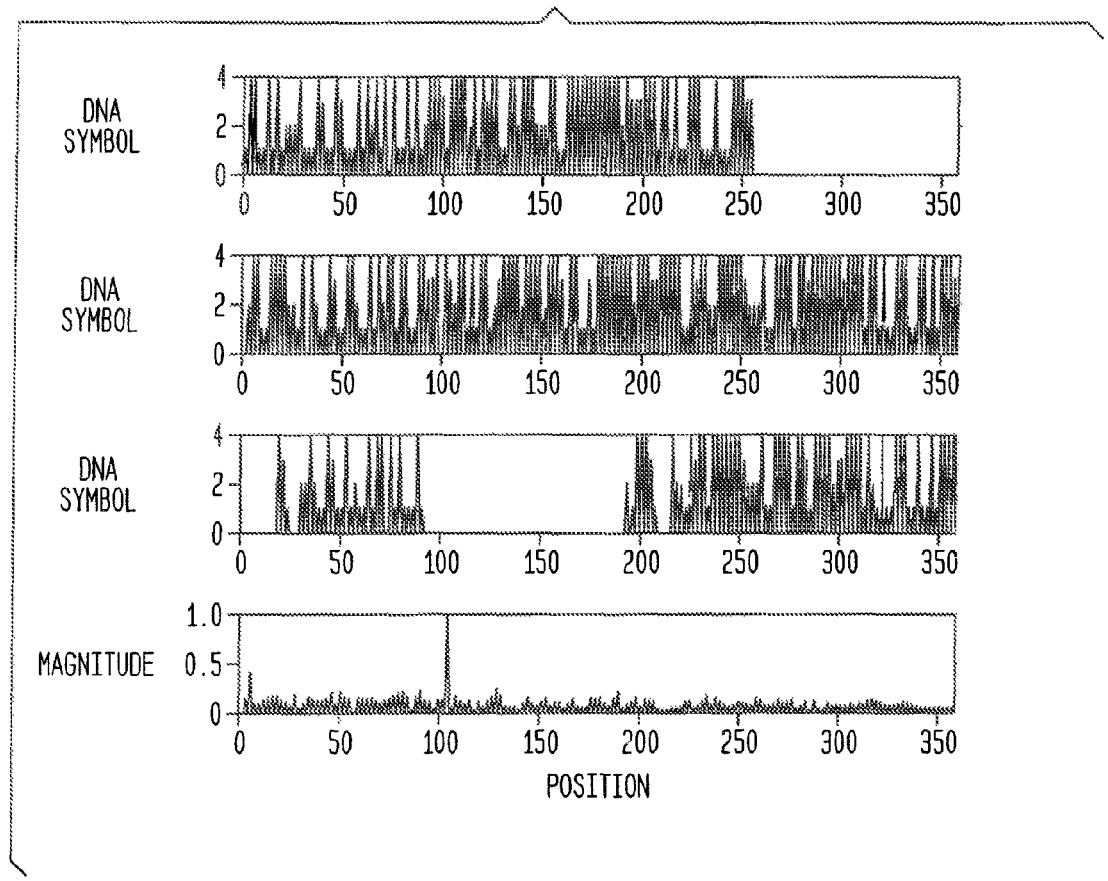
FIG. 8 illustrates plots relating to local alignment of two homologous fruit fly sequences.

In the last experiment, we have performed an alignment of two homologous sequences of satellite DNA molecules from the fruit fly. The data has been described in M. Carlson and D. Brutlag, "Different regions of a complex satellite DNA vary in size and sequence of the repeating unit," *J. Mol. Biol.*, vol. 135, pp. 483-500, 1979, and analyzed in J. Gregor and M. G. Thomason, "Dynamic programming alignment of sequences representing cyclic patterns," *IEEE Trans. Pattern Anal. Mach. Intell.*, vol. 15, no. 2, pp. 129-135, February 1993. The example demonstrates the efficacy of the SPOMF algorithm in the alignment of two- and three-segment weakly semiperiodic DNA sequences, with 76% homology in the two matching segments. The first sequence, GenBank J01125, was 253 bp long, and contained two segments. The second sequence, GenBank V00225, was 359 bp long, and contained three segments. The first and last segments of both sequences were roughly matched. No significant periodic component was present in either sequence. Results of the alignment are shown in FIG. 8. The SPOMF approach produced two peaks in the cross correlation sequence corresponding to sequence shifts $S_1=6$ and $S_2=105$ (plot 808 in FIG. 8). The third plot 806 in FIG. 8 shows (appropriately shifted by $S_1$ and $S_1+S_2$) the matching segments of the first sequence, produced by the local alignment algorithm. The first segment starts at base 27 and ends at base 90 (relative to the second sequence). The second segment starts at base 215 and ends at base 357. Neither of the two segments of the first sequence matches exactly the segments of the second sequence; in both cases there are multiple single and double symbol mismatches. Moreover, the matching segments are preceded by 20- and 25-base-long minisegments that match the second sequence very poorly (the matching strings "t.a" and "ca . . . tttttg . . . a", respectively). Despite the relatively large number of mismatching symbols in the two segments, the SPOMF approach succeeds in producing a local alignment of the two sequences.

6. Comparison of SPOMF and BLAST

The validation part of this work focused on performance comparison of the SPOMF approach with the matched filter (MF) technique. The latter was previously considered by several researchers, and its advantages and disadvantages vis à vis the standard methods were discussed. It has been acknowledged that the principal advantage of the Fourier-based MF approach is its computational efficiency. Moreover, the MF approach 1) is easily adoptable to include certain frequently performed sequence manipulation tasks, such as symbol repetition detection and filtering, 2) can reuse computations from the identical base search in the search of complementary bases, and 3) can be extended to an efficient multiple sequence alignment procedure. On the other hand, the utility of the Fourier-based MF approach is limited by a number of obstructions. These include the inabilities to align sequences with gaps, to differentiate between contiguous and noncontiguous patterns, and to produce a local alignment. While these obstructions are inherent in the direct implementation of MF, work has been performed directed to mediating these obstructions by various adaptations of the MF algorithm. Recently, some work indicates that the last two of these problems might be partly overcome by windowing the query sequence.

The SPOMF of the present invention represents an alternative approach. It was shown above that much of the difficulty in obtaining a local alignment derives from the occurrence of ambiguous sidelobes in the cross correlation sequence. Subsequently, it was demonstrated that the SPOMF substantially reduces these sidelobes, thus improving readability of the global alignment plot, and facilitating the local alignment procedure. The SPOMF approach can be used alternatively or complementarily to the windowing approach.

The differences between methods have been previously discussed in computational molecular biology literature; however, since the Fourier-based approach is not, in general, as well known as some other sequence alignment techniques, especially the industry standard, BLAST, a limited comparison of the two methods can be useful. This is not an easy task. First, the two approaches are based on two very different philosophies. BLAST uses a heuristic search to identify local matches, evaluates symbol similarity according to statistical significance, and focuses on short strings, which are subsequently extended to longer segments. MF and SPOMF, on the other hand, while very different as described herein, are similar in that they exhaustively search for the best global match, do not, in general, use statistical criteria in ranking of alignment scores, and perform computations of all alignments at once. Second, both resolution and efficiency of BLAST, while considered to be well balanced, when compared with other sequence alignment tools, depends on many parameters and on the data. Hence, theoretical computational complexity bounds for BLAST are difficult to obtain, and results of experimental evaluations can be misleading. In effect, a comparison of the two approaches has to be limited and the results tentative.

Nevertheless, we have attempted to draw some inferences about the relative advantages and disadvantages of the two methods. Since the performance issues were addressed in previous section, we decided to focus on computational efficiency.

We have chosen from the BLAST family the fastest program, called MegaBLAST, which has been designed for a rapid comparison of large, closely related sequences. Furthermore, also for efficiency, we have set the MegaBLAST parameters to perform unfiltered (–F F) and ungapped (–g F) search. Since BLAST, unlike SPOMF, does not compare two sequences directly in its entirety, but instead selects a short, adjustable-length fragment from the query sequence, called a seed, running BLAST requires specifying the seed length. We have chosen the two most often used seed sizes, 11 and 28 (the later being the longest allowed). Seed size 28 delivers a faster but less sensitive search than seed size 11, since the matching pattern in the library sequence needs to be at least 28 symbols long. For example, when applied to the sequences analyzed in experiment 6 of the previous section, MegaBLAST-11 identified both matching segments, while MegaBLAST-28 detected only the longer, second segment. We have included both versions in our comparison for completeness; however, we found that sensitivity did not play a major role in the results of alignment of relatively long, highly homologous sequences.

Figure 9:
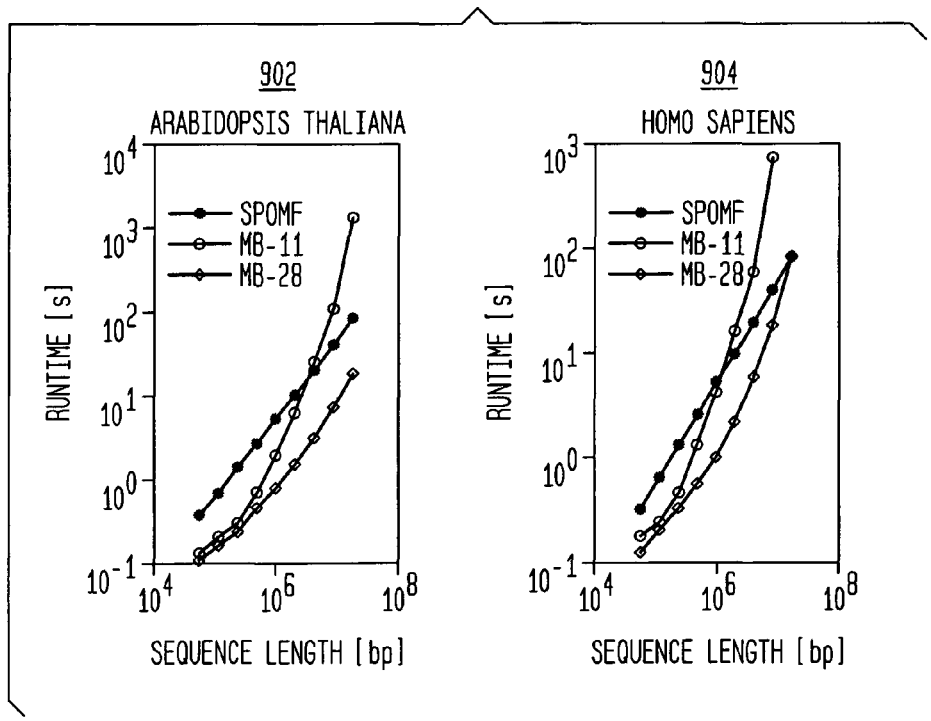
FIG. 9 illustrates sequence alignment runtimes (in seconds) of two versions of BLAST and SPOMF for subsets of *Arabidopsis thaliana* (chromosomes 2 and 4) and *Homo sapiens* (chromosomes 21 and 22).

Experiments were performed on 1.6-GHz Pentium PC with 1 GB of memory, running Microsoft Windows XP. MegaBLAST was run as part of the latest version of the Bl2seq code, obtained from the NCBI website. SPOMF was run in MATLAB 7.0.1 (R14). For the data, we used subsets of sequences *Arabidopsis thaliana* (chromosome 2 and 4) and *Homo sapiens* (chromosome 21 and 22), of lengths ranging from $65 \times 10^3$ to $16 \times 10^6$ bp. The full sizes of the *Arabidopsis thaliana* sequences were 19.6 and $17.5 \times 10^6$ bp; the full sizes of the longest contigs of *Homo sapiens* sequences were 28.6 and $23.3 \times 10^6$ bp, respectively. The results of the experiment are summarized in FIG. 9. Several conclusions can be drawn.

First, the run time and the run time scalability with sequence size of both versions of MegaBLAST are not data independent. For example, the run time of MegaBLAST-28 for *Arabidopsis thaliana* increases almost sixfold with a fourfold increase in sequence length (from $4 \times 10^6$ to $16 \times 10^6$ to bp). In contrast, the run time of MegaBLAST-28 for *Homo sapiens* increases almost fourteenfold for the same sequence lengths. For sequences of length $16 \times 10^6$ bp, the runtimes of MegaBLAST-28 differ by a factor of 5. The dependence of BLAST performance on the data is well known: In A. Das et al., "Performance of Runtime Optimization on BLAST," Dept. of Comp. Sci. and Eng., Univ. of Minnesota, Tech. Rep. TR 04-038, 2004, an example of DNA sequences was given where the run times differed by more than a factor of 100. This is in contrast to SPOMF, whose performance depends solely on the data length. The reasons for the content dependence of BLAST performance are complex, and include, among others, the algorithm's sensitivity to sequence homology.

Second, the performance of MegaBLAST-11 scales very poorly with the sequence length. A fourfold increase in sequence length (from $2 \times 10^6$ to $8 \times 10^6$) leads to a sixteenfold increase in run time for the first sequence, and an almost forty-fivefold increase in run time for the second sequence. In effect, while MegaBLAST-11 can be useful in the analysis of genes and smaller chromosomes, only MegaBLAST-28 and SPOMF are likely to perform well in large searches, such as genomewide alignments. The results of the comparison of these two methods were mixed. For the *Homo sapiens* sequence SPOMF scaled better than MegaBLAST-28, and therefore it is likely to outperform MegaBLAST-28 for sequences longer than $16 \times 10^6$ bp. For the *Arabidopsis thaliana* sequence, both SPOMF and MegaBLAST-28 scaled nearly linearly with the size of the data (although MegaBLAST-28 run times increase faster). As MegaBLAST-28 is roughly four times faster than SPOMF, it can be expected that the phase-only filter will not be competitive with BLAST for sequences of the *Arabidopsis thaliana* type, at least for lengths less than $10^8$ bp.

The results of the experiment do not show a clear efficiency advantage of the SPOMF approach. This is in part due to the limited range of sequence lengths tested. As the rate of increase of computational complexity for both sequences grows faster for BLAST, it can be expected that SPOMF will perform better for sequence lengths in the range of $10^8$ to $10^9$ bp. Also, improvements in implementation of SPOMF will be apparent to persons skilled in the relevant art(s), and such implementation improvements will likely illustrate additional efficiency advantages of SPOMF over BLAST. For example, a future C-code version should improve computational efficiency of SPOMF by making a better use of computer memory. Reductions in the number of required operations due to complex encoding of DNA sequences could further bring at least a twofold improvement in efficiency. Other possible encoding schemes that could be used alternatively or complementarily to the complex encoding include schemes based on gap coding, Huffman coding, and hyper-complex algebra. Also, since FFT is one of the most common tasks in signal processing, computer accelerator cards are commercially available, and can speed up the computation of SPOMF significantly.

7. Operational Summary and Exemplary Computer System Implementation

The invention shall be summarized in this section.

Figure 11:
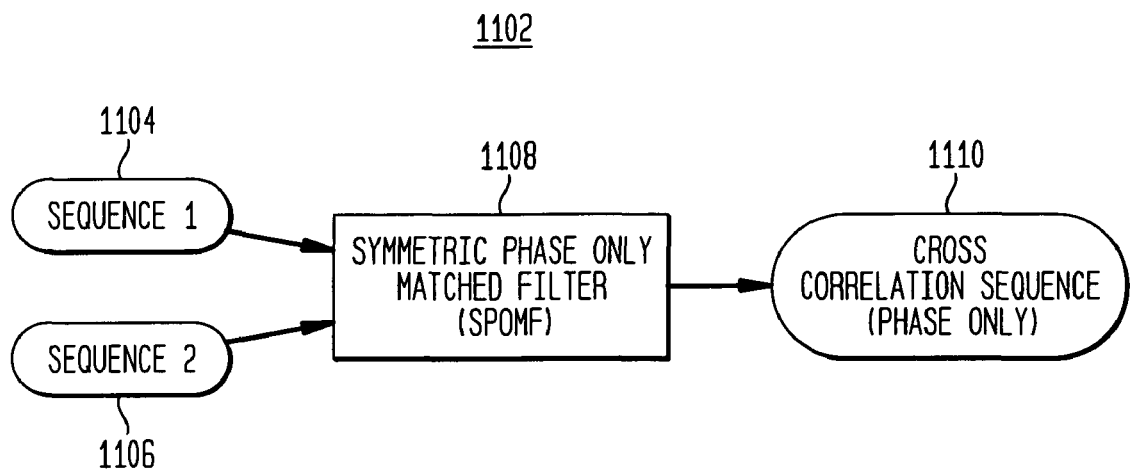
FIG. 11 illustrates a data flow block diagram of a symmetric phase only matched filter, according to an embodiment of the invention.

As described above, the invention is directed to improved systems, methods and computer program products for DNA sequence alignment. Referring to FIG. 11, embodiments of the invention use a symmetric phase only matched filter (SPOMF) 1108 to perform DNA sequence alignment. Operation of the SPOMF 1108 is represented by Equation (5), above, and implementation of the SPOMF 1108 so that it implements Equation (5) will be apparent to persons skilled in the relevant art(s).

As will be appreciated, the numerator of Equation (5) represents magnitude and phase information, whereas the denominator represents only magnitude information. Accordingly, the cross correlation sequence w(n) that results from Equation (5) is based on only phase information. The SPOMF cross correlation sequence w(n) is represented by 1110 in FIG. 11.

Figure 10:
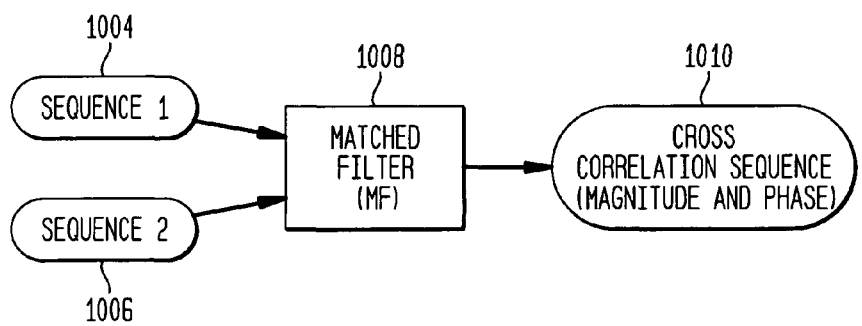
FIG. 10 illustrates a data flow block diagram of a matched filter.

The operation of a matched filter (MF) 1008 (see FIG. 10) is represented by Equation (4). In contrast to the SPOMF 1108, the MF 1008 generates a cross correlation sequence 1010 that is based on both magnitude and phase information. This difference between the SPOMF 1108 and the MF 1008 is a primary reason why the SPOMF 1108 achieves the DNA sequence alignment improvements described herein.

Figure 12:
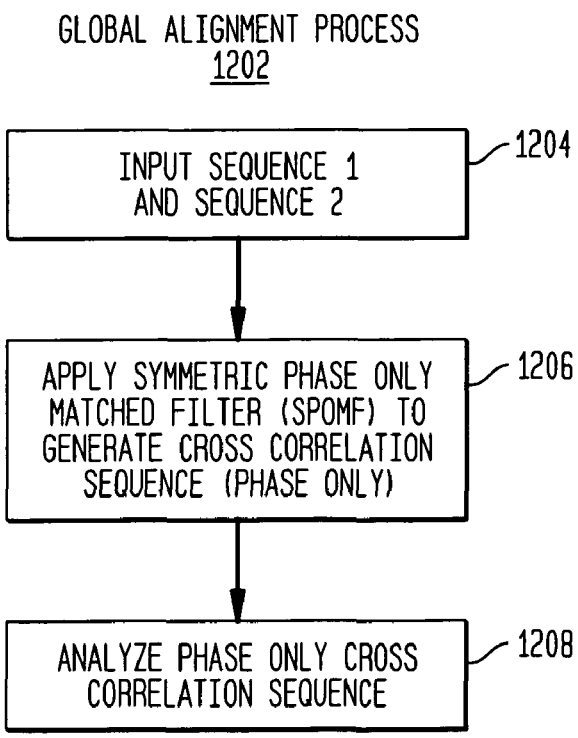
FIG. 12 illustrates a global alignment process using a symmetric phase only matched filter, according to an embodiment of the invention.

FIG. 12 illustrates a global DNA sequence alignment process 1202 according to an embodiment of the invention, which shall now be described with continuing reference to the data flow diagram 1102 of FIG. 11.

In step 1204, sequence 1 and sequence 2 are input to the SPOMF 1108, where sequences 1 and 2 are two discrete DNA sequences.

In step 1206, SPOMF 1108 processes sequences 1 and 2. More particularly, phase only cross correlation sequence 1110 is generated by applying sequences 1 and 2 to Equation 5.

In step 1208, the phase only cross correlation sequence 1110 is analyzed. Options for such analysis of the phase only cross correlation sequence 1110 will be apparent to persons skilled in the relevant art(s) based on the teachings contained herein.

As discussed above, it may be desirable to prevent the denominator in Equation (5) from being zero. The invention includes a number of embodiments for achieving this. In one embodiment, for example, the denominator is prevented from being less than a predetermined minimum value.

Figure 14:
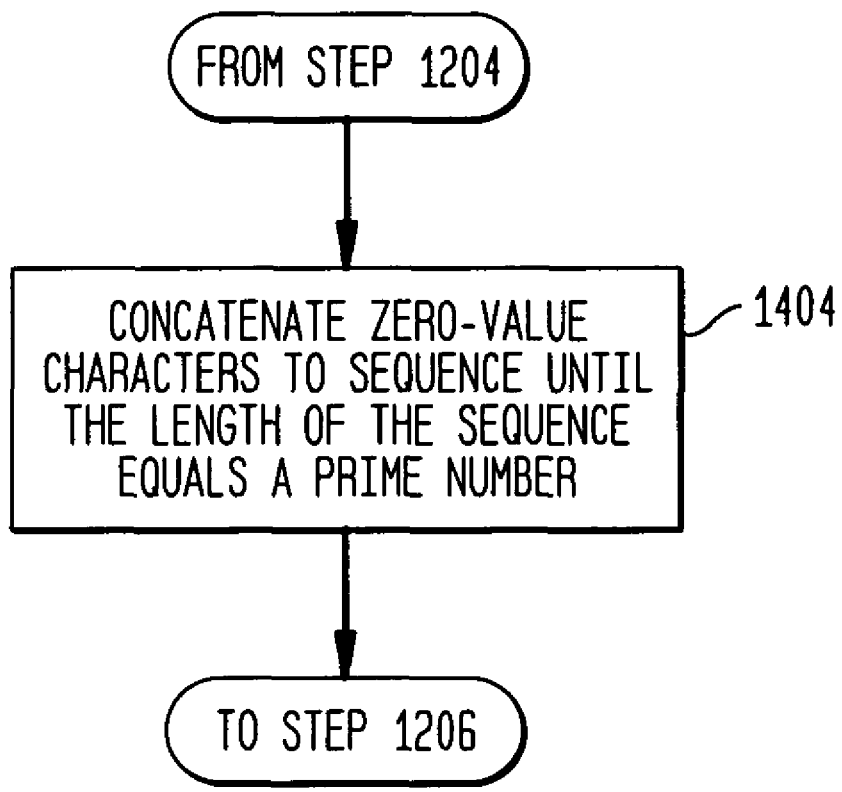
FIG. 14 illustrates a prime-length cross correlation algorithm according to an embodiment of the invention.

In another embodiment, a prime-length cross correlation process is used. According to the prime-length cross correlation process, zero-value characters are added to the sequences represented in the denominator of Equation (5) until the length of such sequences equal a prime number. As described above, by using prime length sequences, a zero value in the denominator of Equation (5) is avoided. Such operation is represented by step 1404 in FIG. 14. In an embodiment, this step 1404 is inserted between steps 1204 and 1208 of FIG. 12, to thereby modify the global alignment process 1202 to a prime-length cross correlation process.

As discussed above, another advantage of the invention is related to local alignment. As is well known, matched filters can not be used for local alignment. In contrast, according to embodiments of the invention, local alignment is performed using SPOMF. A local alignment process using SPOMF according to an embodiment of the invention is illustrated in FIG. 13, which was described above.

It is noted that the SPOMF has been described herein with regard to DNA sequence alignment. However, the invention is not limited to this example embodiment. The SPOMF as described herein is applicable to other sequence alignment applications, not just those involving DNA.

Figure 15:
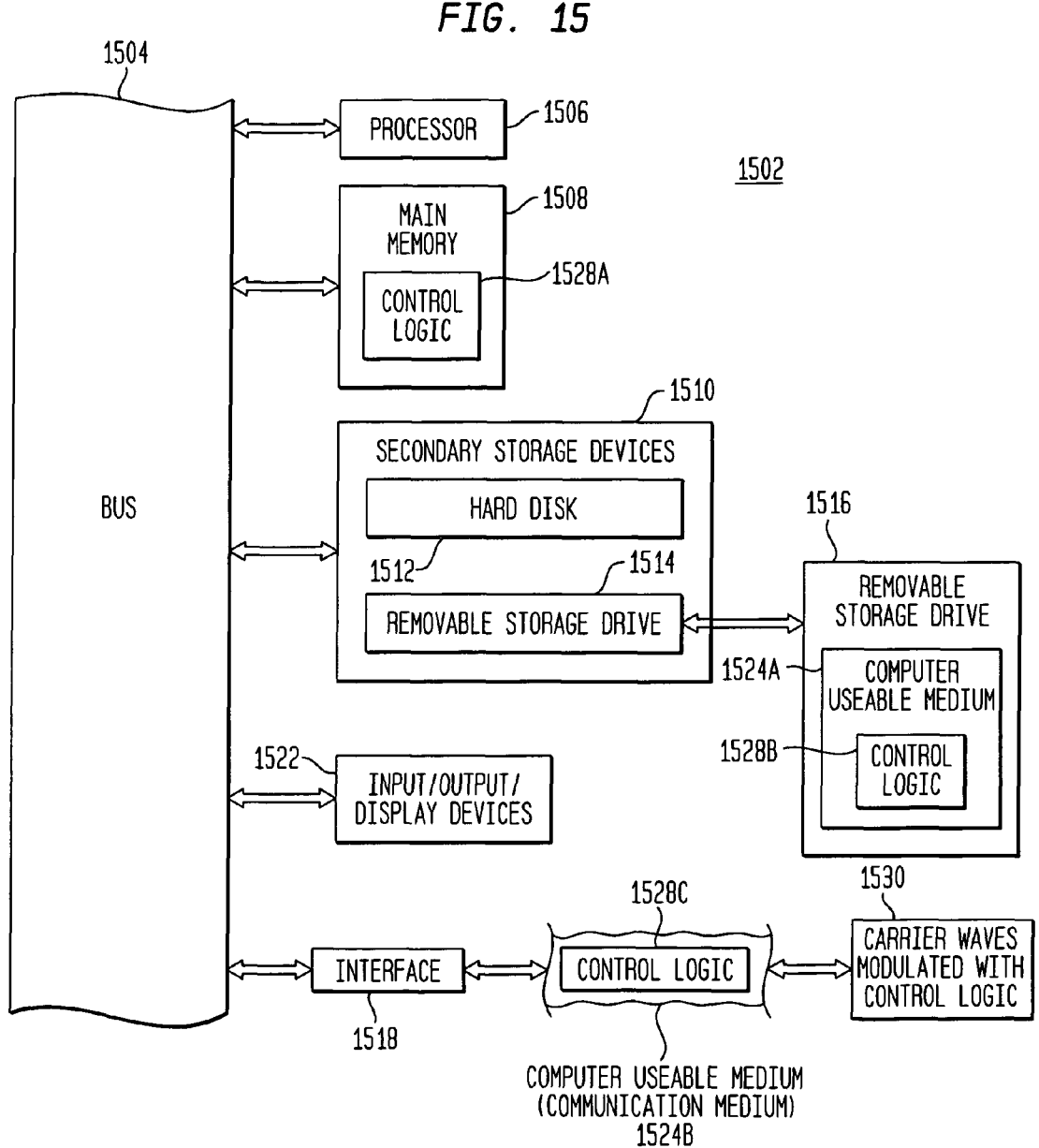
FIG. 15 illustrates a computer system useful for implementing various embodiments of the invention.

In an embodiment of the present invention, the system, components, processes and algorithms of the present invention described herein are implemented using well known computers, such as a computer 1502 shown in FIG. 15. The computer 1502 can be any commercially available and well known computer capable of performing the functions described herein, such as computers available from International Business Machines, Apple, Sun, HP, Dell, Compaq, Digital, etc.

The computer 1502 includes one or more processors (also called central processing units, or CPUs), such as a processor 1506. The processor 1506 is connected to a communication bus 1504.

The computer 1502 also includes a main or primary memory 1508, such as random access memory (RAM). The primary memory 1508 has stored therein control logic 1528A (computer software), and data.

The computer 1502 also includes one or more secondary storage devices 1510. The secondary storage devices 1510 include, for example, a hard disk drive 1512 and/or a removable storage device or drive 1514. The removable storage drive 1514 represents a floppy disk drive, a magnetic tape drive, a compact disk drive, an optical storage device, tape backup, etc.

The removable storage drive 1514 interacts with a removable storage unit 1516. The removable storage unit 1516 includes a computer useable or readable storage medium 1524 having stored therein computer software 1528B (control logic) and/or data. Removable storage unit 1516 represents a floppy disk, magnetic tape, compact disk, DVD, optical storage disk, or any other computer data storage device. The removable storage drive 1514 reads from and/or writes to the removable storage unit 1516 in a well known manner.

The computer 1502 also includes input/output/display devices 1522, such as monitors, keyboards, pointing devices, etc.

The computer 1502 further includes a communication or network interface 1518. The network interface 1518 enables the computer 1502 to communicate with remote devices. For example, the network interface 1518 allows the computer 1502 to communicate over communication networks or mediums 1524B (representing a form of a computer useable or readable medium), such as LANs, WANs, the Internet, etc. The network interface 1518 may interface with remote sites or networks via wired or wireless connections.

Control logic 1528C may be transmitted to and from the computer 1502 via the communication medium 1524B. More particularly, the computer 1502 may receive and transmit carrier waves (electromagnetic signals) modulated with control logic 1530 via the communication medium 1524B.

Any apparatus or manufacture comprising a computer useable or readable medium having control logic (software) stored therein is referred to herein as a computer program product or program storage device. This includes, but is not limited to, the computer 1502, the main memory 1508, the hard disk 1512, the removable storage unit 1516 and the carrier waves modulated with control logic 1530. Such computer program products, having control logic stored therein that, when executed by one or more data processing devices, cause such data processing devices to operate as described herein, represent embodiments of the invention.

The invention can work with software, hardware, and/or operating system implementations other than those described herein. Any software, hardware, and operating system implementations suitable for performing the functions described herein can be used.

8. Conclusion

While various embodiments of the present invention have been described above, it should be understood that they have been presented by way of example only, and not limitation. It will be understood by those skilled in the relevant art(s) that various changes in form and details may be made therein without departing from the spirit and scope of the invention as defined in the appended claims. Accordingly, the breadth and scope of the present invention should not be limited by any of the above-described exemplary embodiments, but should be defined only in accordance with the following claims and their equivalents.

What is claimed is:

1. A method of aligning segments in two sequences, comprising:
performing using at least one processing device:
generating a phase only cross correlation sequence between numeric sequences x and y, wherein the phase only cross correlation sequence includes peaks that are not obscured by sidelobes;
identifying two distinct peaks in the phase only cross correlation sequence;
setting variables $S_1$ and $S_2$ to positions of the two distinct peaks;
forming auxiliary sequences $y_1(n)=y(n-S_1)$ and $y_2(n)$ $y(n-S_2)$;
computing pointwise products $z_1=xy_1$ and $x_2=xy_2$;
identifying a contiguous segment of non-negative values in sequence $z_1$ as a first segment;
identifying a contiguous segment of non-negative values in sequence $z_2$ as a second segment; and
aligning the first and second segments by shifting the first and second segments by $S_1$ and $S_2$.

2. The method of claim 1, wherein the numeric sequences x and y are numerical mappings of DNA sequences.

3. The method of claim 1, further comprising computing the equation $$w(n) = DFT^{-1}\left\{\frac{x(k)\overline{y}(k)}{|x(k)\overline{y}(k)|}\right\},$$

wherein w(n) is the phase only cross correlation sequence between x and y, x(k) and y(k) are respectively discrete Fourier transforms of the numeric sequences x and y, and $DFT^{-1}\{\cdot\}$ is an inverse discrete Fourier transform.

4. The method of claim 3, further comprising, prior to the calculation of w(n), concatenating zero-value symbols to sequences x(k) and y(k) until a length of sequence x(k) is a prime number and a length of sequence y(k) is a prime number.

5. A system for aligning segments in two sequences, comprising:
at least one processing device; and
instructions that cause the at least one processing device to:
generate a phase only cross correlation sequence between numeric sequences x and y, wherein the phase only cross correlation sequence includes peaks that are not obscured by sidelobes;

identify two distinct peaks in the phase only cross correlation sequence;

set variables $S_1$ and $S_2$ to positions of the two distinct peaks;

form auxiliary sequences $y_1(n)=y(n-S_1)$ and $y_2(n)=y(n-S_2)$;

compute pointwise products $z_1=xy_1$ and $x_2=xy_2$;

identify a contiguous segment of non-negative values in sequence $z_1$ as a first segment;

identify a contiguous segment of non-negative values in sequence $z_2$ as a second segment; and align the first and second segments by shifting the first and second segments by $S_1$ and $S_2$.

6. The system of claim 5, wherein the numeric sequences x and y are numerical mappings of DNA sequences.

7. The system of claim 5, further comprising instructions that cause the at least one processing device to compute the equation $$w(n) = DFT^{-1}\left\{\frac{x(k)\bar{y}(k)}{|x(k)\bar{y}(k)|}\right\},$$

wherein w(n) is the phase only cross correlation sequence between x and y, x(k) and y(k) are respectively discrete Fourier transforms of the numeric sequences x and y, and $DFT^{-1}\{\cdot\}$ is an inverse discrete Fourier transform.

8. The system of claim 7, further comprising instructions that cause the at least one processing device to, prior to the calculation of w(n), concatenate zero-value symbols to sequences x(k) and y(k) until a length of sequence x(k) is a prime number and a length of sequence y(k) is a prime number.

9. A non-Transitory computer-readable storage device having instructions stored thereon, execution of which, by a processing device, causes the processing device to perform operations comprising:

generating a phase only cross correlation sequence between numeric sequences x and y, wherein the phase only cross correlation sequence includes peaks that are not obscured by sidelobes;

identifying two distinct peaks in the phase only cross correlation sequence;

setting variables $S_1$ and $S_2$ to positions of the two distinct peaks;

forming auxiliary sequences $y_1(n)=y(n-S_1)$ and $y_2(n)-S_2$);

computing pointwise products $z_1=xy_1$ and $x_2\, xy_2$;

identifying a contiguous segment of non-negative values in sequence $z_1$ as a first segment;

identifying a contiguous segment of non-negative values in sequence $z_2$ as a second segment; and aligning first and second segments by shifting the segments by $S_1$ and $S_2$.

10. The non-transitory computer-readable storage device of claim 9, wherein the numeric sequences x and y are numerical mappings of DNA sequences.

11. The non-transitory computer-readable storage device of claim 9, the operations further comprising computing the equation $$w(n) = DFT^{-1}\left\{\frac{x(k)\bar{y}(k)}{|x(k)\bar{y}(k)|}\right\},$$

wherein w(n) is the phase only cross correlation sequence between x and y, x(k) and y(k) are respectively discrete Fourier transforms of the numeric sequences x and y, and $DFT^{-1}\{\cdot\}$ is an inverse discrete Fourier transform.

12. The non-transitory computer-readable storage device of claim 11, the operations further comprising, prior to the calculation of w(n), concatenating zero-value symbols to sequences x(k) and y(k) until a length of sequence x(k) is a prime number and a length of sequence y(k) is a prime number.

* * * * *